United States Patent [19]

Ohyama et al.

[11] Patent Number: 5,384,426

[45] Date of Patent: Jan. 24, 1995

[54] PROCESS FOR THE PREPARATION OF ISOPROPYL ACETATE

[75] Inventors: Kyuichi Ohyama, Ohtake; Giichi Shimada, Iwakuni; Yuichi Tokumoto, Yokohama; Kazuo Sakamoto, Zama, all of Japan

[73] Assignee: Daicel Chemical Industries, Ltd., Sakai, Japan

[21] Appl. No.: 163,304

[22] Filed: Dec. 7, 1993

[30] Foreign Application Priority Data

Dec. 8, 1992 [JP] Japan .................................. 4-351915

[51] Int. Cl.6 .............................................. C07C 67/04
[52] U.S. Cl. ........................................................ 560/247
[58] Field of Search ......................................... 560/247

[56] References Cited

U.S. PATENT DOCUMENTS

| | | | |
|---|---|---|---|
| 1,863,135 | 12/1931 | Suida | 560/247 |
| 1,877,291 | 9/1932 | Frolich | 560/247 |
| 2,021,851 | 11/1935 | Coleman | 560/247 |
| 2,042,218 | 5/1936 | Evans | 560/247 |
| 2,224,809 | 12/1940 | Coleman | 560/247 |
| 2,414,999 | 1/1947 | Bearse | 560/247 |
| 2,678,332 | 5/1954 | Cottle | 560/247 |
| 2,740,800 | 4/1956 | Mention | 560/247 |
| 3,053,887 | 9/1962 | Aries | 560/247 |
| 3,055,934 | 9/1962 | Heisler | 560/247 |
| 3,102,905 | 9/1963 | Wheeler | 560/247 |
| 3,299,110 | 1/1967 | Pine | 560/247 |
| 3,474,131 | 10/1969 | Schmerling | 560/247 |
| 3,922,294 | 11/1975 | Leupold | 560/247 |

*Primary Examiner*—Michael L. Shippen
*Attorney, Agent, or Firm*—Morgan & Finnegan

[57] ABSTRACT

Disclosed is an improved process for the refinement of isopropyl acetate, whereby there can be effectively prepared isopropyl acetate having a high purity of, for example, approximately 99.9%, in which a distillate fraction having a carbon number of 3 obtained by catalytically cracking petroleums such as naphtha or a crude propylene by-produced in a process for the preparation of isobutene by the dehydrogenation of isobutane.

8 Claims, 1 Drawing Sheet

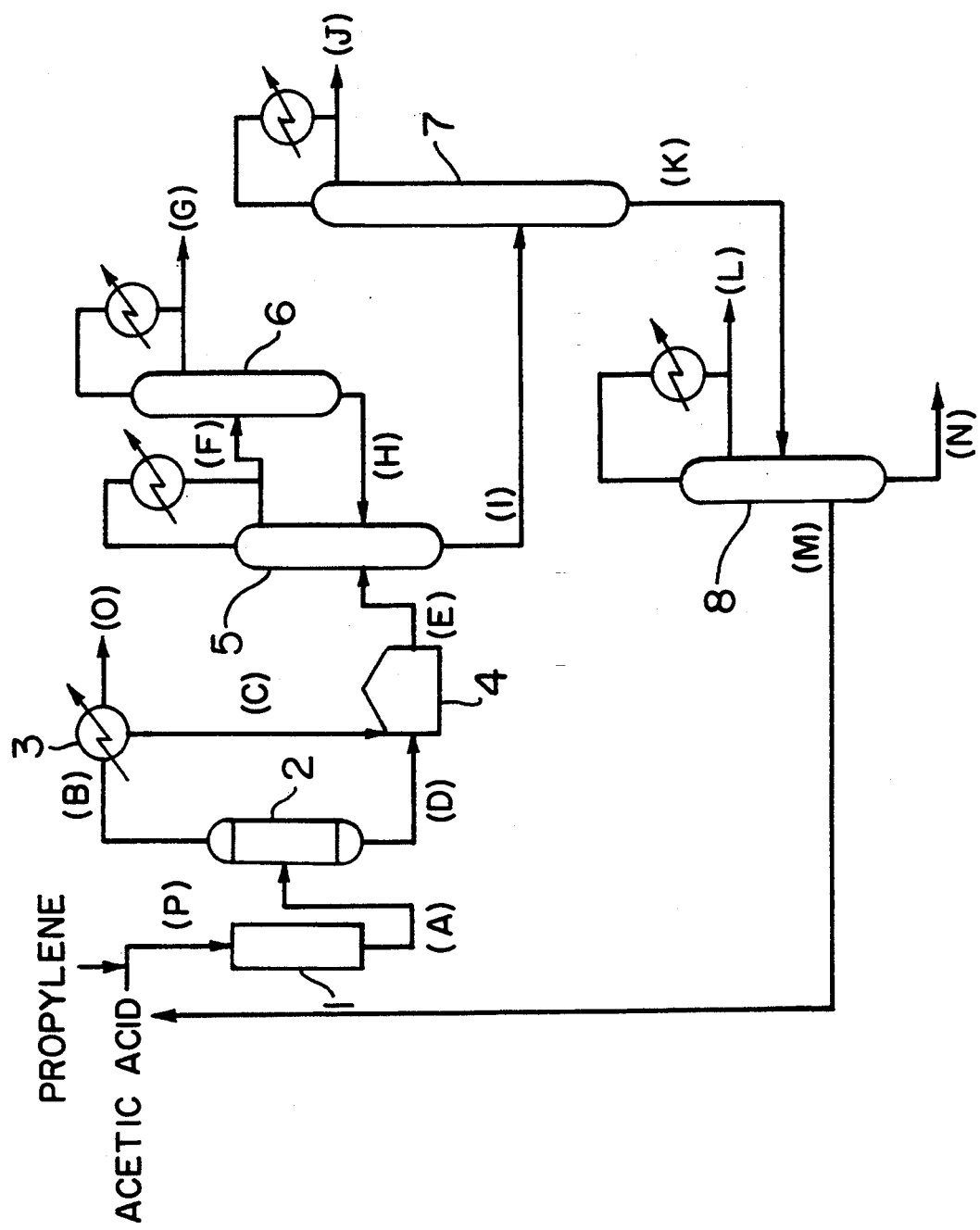

PROCESS FOR THE PREPARATION OF ISOPROPYL ACETATE

FIELD OF THE INVENTION

The present invention relates to a process for the preparation of isopropyl acetate.

In particular, the present invention relates to an improved process for the refinement of isopropyl acetate, whereby there can be effectively prepared isopropyl acetate having a high purity, namely of, for example, approximately 99.9%, in which there can be used a distillate fraction having a carbon number of 3 which is obtained by catalytically cracking petroleums such as naphtha or a crude propylene which is obtained as a by-product in a process for the preparation of isobutene by the dehydrogenation of isobutane.

BACKGROUND OF THE INVENTION

Isopropyl acetate is a compound which is useful as a solvent or as a material for preparing perfumes.

It is known that isopropyl acetate can be prepared in a liquid phase reaction of acetic acid with propylene in the presence of an acidic ion-exchange resin catalyst [eg. Japanese Patent Unexamined Publication(Kokai) No. 169552/19923], through the following equation.

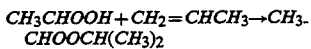

$$CH_3CHOOH + CH_2 = CHCH_3 \rightarrow CH_3CHOOCH(CH_3)_2$$

Furthermore, it is known that unreacted acetic acid is recirculated in an industrial process for the preparation of isopropyl acetate in order to increase the overall yield(eg. Hydrocarbon processing, Apr. 1975).

A hydrocarbon mixture containing above 20% by weight of propylene is preferably used in the industrial process for the preparation of isopropyl acetate as a starting propylene having impurities from the view point of cost.

The hydrocarbon mixture includes a distillate fraction having a carbon number of 3 which is obtained by catalytically cracking petroleums such as a naphtha or a crude propylene which is obtained as a by-product in a process for the preparation of isobutene by the dehydrogenation of isobutane, as the starting propylene having impurities.

However, in the case that the above-mentioned crude propylene is used, isopropyl alcohol(boiling point of 82° C.), etc. are produced as a by-product in the reaction of propylene with small amounts of water which is contained in the starting crude propylene and acetic acid.

Small amounts of water is also inevitably produced with the generation of acetic anhydride from acetic acid.

Furthermore, olefins having a carbon number of 7 and acetates having a carbon number of above 6 are produced as by-products by the reaction of the impurities(olefins having a carbon number of 4) in the starting materials with propylene and acetic acid, respectively.

The by-products have boiling points that are close to those of isopropyl acetate and acetic acid, resulting in that there is difficult to separate by distillation.

Accordingly, conventional arrangements of continuous distillation columns would increase the cost of equipment due to the necessity of many plates in the distillation columns, which, if not used, would result in an increased loss of isopropyl acetate.

The above process has many problems and is, therefore, not practical as an industrial process.

Given these circumstances, there has been much demand for a process for the preparation of isopropyl acetate having a high purity using the above-mentioned crude propylene, and as a result of the studies performed by the present inventors, the present invention has been completed.

SUMMARY OF THE INVENTION

An object of the present invention is to provide a process for the preparation of isopropyl acetate having a high purity with a high yield.

An aspect of the present invention is a process for the preparation of isopropyl acetate by the reaction of propylene having impurities with acetic acid which comprises the following steps:

(a) separating a reaction mixture obtained in a reaction system into gas phase and liquid phase;

(b) cooling said gas phase to separate into a condensate and a non-condensate;

(c) mixing said condensate with said liquid phase to make a reaction crude mixture, and then charging said reaction crude mixture into a first distillation column to separate into a column-top-mixture having low-boiling-point ingredients and a column-bottom-mixture having high-boiling-point ingredients;

(d) charging said column-top-mixture into a second distillation column to obtain a column-top-mixture containing low-boiling-point ingredients and a column-bottom-mixture containing isopropyl acetate;

(e) recirculating said column-bottom-mixture in the second distillation column to the first distillation column while distilling off said column-top-mixture;

(f) charging said column-bottom-mixture in the second distillation column into a third distillation column to obtain a column-top-mixture consisting essentially of isopropyl acetate and a column-bottom-mixture containing acetic acid and high-boiling-point ingredients;

(g) charging said column-bottom-mixture in the third distillation column into a fourth distillation column to distill off a column-top-mixture containing minor amounts of acetic acid while recirculating a side-stream-mixture containing acetic acid to said reaction system and discharging a column-bottom-mixture containing high-boiling-point ingredients.

BRIEF DESCRIPTION OF THE DRAWINGS

FIG. 1 is a block diagram illustrating a process for the preparation of isopropyl acetate having a high purity.

Here, numbers 1, 2, 3 and 4 are a reaction vessel, a flush tank, a condenser and a reservoir, respectively, and numbers 5, 6, 7 and 8 are a first distillation column, a second distillation column, a third distillation column and a fourth distillation column, respectively.

DETAILED DESCRIPTION OF THE INVENTION

The present invention is described hereinafter in more detail based on accompanying FIG. 1.

In accordance with an aspect of the present invention, there is provided a process for the preparation of isopropyl acetate having a high purity by the reaction of propylene having impurities with acetic acid which comprises the following steps (a) to (g) below;

(a) separating a reaction mixture obtained in a reaction system into gas phase and liquid phase;

(b) cooling said gas phase to separate into a condensate and a non-condensate;

(c) mixing said condensate with said liquid phase to make a reaction crude mixture, and then charging said reaction crude mixture into a first distillation column to separate into a column-top-mixture having low-boiling-point ingredients and a column-bottom-mixture having high-boiling-point ingredients;

(d) charging said column-top-mixture into a second distillation column to obtain a column-top-mixture containing low-boiling-point ingredients and a column-bottom-mixture containing isopropyl acetate;

(e) recirculating said column-bottom-mixture in the second distillation column to the first distillation column while distilling off said column-top-mixture;

(f) charging said column-bottom-mixture in the second distillation column into a third distillation column to obtain a column-top-mixture consisting essentially of isopropyl acetate and a column-bottom-mixture containing acetic acid and high-boiling-point ingredients;

(g) charging said column-bottom-mixture in the third distillation column into a fourth distillation column to distill off a column-top-mixture containing minor amounts of acetic acid while recirculating a side-stream-mixture containing acetic acid to said reaction system and discharging a column-bottom-mixture containing high-boiling-point ingredients.

FIG. 1 is a block diagram that shows a process for the preparation of isopropyl acetate in which the steps, (a) to (g), are combinedly shown.

In FIG. 1, numbers 1, 2, 3 and 4 are a reaction vessel, a flush tank, a condenser and a reservoir, respectively, and numbers 5, 6, 7 and 8 are a first distillation column, a second distillation column, a third distillation column and a fourth distillation column, respectively.

An arrow shows the stream direction of the solution or gas, and letters (A) to (P) show the solution or gas streaming therethrough.

In the present invention, the starting mixture(A) containing isopropyl acetate is firstly prepared by the reaction of propylene having impurities with acetic acid in the presence Of a catalyst in the reaction vessel (1). The propylene having impurities which is one starting material includes a crude propylene obtained by catalytically cracking petroleums such as naphtha and a crude propylene by-produced in a process for the preparation of isobutene by dehydrogenation of isobutane.

The former crude propylene primarily contains propylene, propane and olefins having a carbon number of 4, etc. The latter crude propylene primarily contains propylene, methane, ethane, propane, isobutane, ethylene and olefins having a carbon number of 4, etc.

Furthermore, the reaction system contains small amounts of water derived from the crude propylene and acetic acid and inevitably produced with the generation of acetic anhydride from acetic acid by a side reaction in the reaction of propylene with acetic acid.

The catalyst is to be selected from catalysts commonly used in reactions of this kind, which are not particular catalysts.

Acidic catalysts such as an acidic ion-exchange resin are generally used, and the reaction can be carried out in a liquid phase, gas phase or a mixed phase composed of gas phase and liquid phase.

The acetic acid having small amounts of water and propylene having impurities which are starting materials(P) are preferably fed through parallel liquid-phase streams into the continuous-flow fixed-bed reaction vessel(1) in which an acidic ion-exchange resin is packed as a catalyst.

The molar ratio of acetic acid to propylene is preferably within a range of from 1.0 to 2.0.

The internal pressures in the reaction vessel are suitably maintained to within a range of 15 to 100 kg/cm$^2$, preferably 15 to 50 kg/cm$^2$ which is sufficient to keep the reaction system in a liquid state.

The reaction is carried out while maintaining the temperature of the area around the inlet of the catalyst bed to within the range of 70° to 120° C.

The crude reaction mixture(A) containing isopropyl acetate obtained in the reaction is used as a starting material in the present invention.

The crude reaction mixture(A) is usually fed in a pressurized state into a flush tank(2), and then depressurized back to atmospheric pressure. In the flush tank(2), a liquid phase(D) and a gas phase(B) are separated from each other. The gas phase(B) is cooled through a condenser(3) in order to recover isopropyl acetate, this minimizes the loss of isopropyl acetate that occurs in flushing.

A gas phase(0) discharged from the condenser(3) primarily contains propylene and inert gases such as methane, propane, butane and carbondioxide, etc. which are usually disposed of as waste gases.

It is noted that in the case that propylene containing large amounts of the inert gases is used, the wastegases(O) volume increases.

The temperature of the coolant to be used in the condenser(3) is preferably not more than 20° C.

A condensate(C) containing isopropyl acetate in the condenser(3) is mixed with a liquid phase(D) in a tank(4), and the mixture(E) is continuously charged into the first distillation column(5).

The first distillation column(5) is installed for the purpose of removing low-boiling-point ingredients(F) which include isopropyl acetate, isopropyl alcohol, isopropyl ethers and olefins having a carbon number of 7 which are impurities produced in the present reaction conditions.

The olefins having a carbon number of 7 contained in the low-boiling-point ingredients(F) are produced by the reaction of propylene with olefins having a carbon number 4.

The olefins having a carbon number of 7 mainly cause a deterioration in the purity of isopropyl acetate which is the desired product.

Therefore, the removal of the above-mentioned low-boiling-point ingredients(F) is conducted in the first distillation column(5) for the purpose of preparing isopropyl acetate having purity of 99.9% or so at a high yield.

Isopropyl alcohol and isopropyl ether are produced as by-products by the reaction of propylene with the above-mentioned small amount of water.

Although the operating conditions in the first distillation column(5) are selected so that the above-mentioned low-boiling-point ingredients in a mixture(I) from the bottom of the first distillation column(5) are decreased to a regulated concentration, the olefins having a carbon number of 7 are not readily separated from isopropyl acetate because of the close boiling points in the two.

Accordingly, unnecessarily large amounts of isopropyl acetate would be forced to distill off together with isopropyl alcohol, isopropyl ether and olefins having a carbon number of 7.

If the above-mentioned low-boiling-point ingredients(F) were disposed of without any treatment, the yield of isopropyl acetate which is the desired product inevitably would be decreased.

In order to prevent a lowering of the yield, the low-boiling-point ingredients(F) are charged into the second distillation column(6) to recover isopropyl acetate therefrom.

The mixture(H) discharged from the bottom of the second distillation column(6) which includes isopropyl acetate and small amounts of low-boiling-point ingredients is charged into a reasonable stage in the first distillation column(5), that is, a multi-stage process is conducted, resulting in that the loss of isopropyl acetate can be remarkably decreased.

The reasonable stage means a middle portion in the first distillation column(5) near which the mixture(E) is charged.

It is noted that the volume of the low-boiling-point ingredients(F) charged into the second distillation column(6) is approximately 1/20 of the volume of the above-mentioned mixture(E).

Accordingly, the second distillation column(6) may have the diameter of not more than 1/3 compared to the first distillation column(5), in order to keep engineering and operation costs to a minimum.

A distillate(G) discharged from the top of the second distillation column(6) is usually burned as a waste.

Successively, the mixture(I) discharged from the bottom of the first distillation column(5) is charged into the third distillation column(7) to obtain from the column top isopropyl acetate(J) which is the desired product. The mixture(K) discharged from the bottom of the third distillation column(7) is charged into the side portion of the fourth distillation column(8).

The mixture(K) primarily contains acetic acid which is an unreacted starting material, sec-butyl acetate and high-boiling-point ingredients.

In the fourth distillation column(8), the high-boiling-point ingredients(N) and a mixture(L) which primarily contains acetic acid and olefins having a carbon number of 9 are removed to recover a mixture(M) which primarily contains the unreacted acetic acid and sec-butyl acetate.

The mixture(M) is discharged from a portion lower than the side portion to charge the mixture(K), and the mixture(M) is recirculated into the reaction system(1).

Minor amounts of acetic acid in the mixture(L) which is an azeotropic mixture is discharged together with olefins having a carbon number of 9 and very minor amounts of isopropyl acetate as a waste.

Sec-butyl acetate is produced by the reaction of acetic acid with olefins having a carbon number of 4 which are impure ingredients in the starting crude propylene. The boiling point of sec-butyl acetate is close to the boiling point of acetic acid, resulting in both being difficult to separate from each other by distillation.

However, it was confirmed that sec-butyl acetate in the mixture(M) is decomposed in the reaction vessel(1) to produce acetic acid and olefins having a carbon number of 4, and that sec-butyl acetate does not increase while passing through all of the stages. Accordingly, it is not required that sec-butyl acetate is separated from acetic acid.

The mixture(K) contains acetic acid, olefins having a carbon number of 9 which exist primarily in the form of trimers of propylene, esters of olefins having a carbon number of 9 and minor amount of isopropyl acetate.

The olefins having a carbon number of 9 would produce an azeotropic mixture with acetic acid, resulting in that acetic acid is incapable of being separated from the olefins having a carbon number of 9 by distilling off acetic acid from the top of the distillation column and discharging the olefins having a carbon number of 9.

It appears that the esters of olefins having a carbon number of 9 are produced by the addition reaction of acetic acid to the olefins having a carbon number of 9.

It is preferred from the view point of cost that acetic acid is recovered and recirculated into the reaction vessel.

Nevertheless, if acetic acid containing the olefins having a carbon number of 9 is compulsorily recirculated into the reaction vessel, the olefins would be accumulated through the reaction system and distillation system, or large amounts of useless by-products would be produced.

Furthermore, it is thought that the catalysts are adversely affected.

To prevent this, the concentrated olefins would have to intermittently removed from the continuous distillation system, which makes the operation difficult to control.

In order to avoid the above difficulties, a mixture(L) primarily composed of the olefins having a carbon number of 9 and acetic acid is distilled off from the top of the fourth distillation column(8) by making use of the azeotropic property between acetic acid and the olefins, and the high-boiling-point ingredients(N) containing acetates, etc. are discharged from the bottom of the fourth distillation column(8).

The mixture(M) which includes acetic acid and sec-butyl acetate is discharged from the side portion of the fourth distillation column(8), whereby acetic acid not containing undesirable impurities can be recovered.

As the result, only small amounts of acetic acid are lost in the azeotropic mixture(L).

In the following, although examples are described in order to more specifically illustrate the present invention, the present invention is not limited to the examples in the Examples section below.

EXAMPLE 1

A mixture(P) composed of acetic acid having below 0.1% of water and a crude propylene which contains 76.1% of propylene, 22.0% of propane and 1.9% of olefins having a carbon number of 4, etc. was supplied into a tube-typed reaction vessel(1) shown in FIG. 1, in which also an acidic ion-exchange resin was placed as a catalyst.

The mixture (P) was allowed to react while passing through the catalyst layer, after which it was cooled while being partially recirculated through a heat exchanger(not shown in FIG. 1).

Acetic acid was supplied into the reaction vessel(1) at an LHSV (quantity of feed current to the catalyst) of acetic acid relative to the catalyst layer of 1.0, acetic acid/propylene molar ratio of 1.4 and a reaction pressure of 40 kg/cm$^2$.

The pressurized reaction crude solution obtained was discharged into a flush tank(2) to separate it into a gas phase mixture(B)[non-condensation ingredients] and a liquid phase mixture(D)[condensation ingredients].

The non-condensation ingredients(B) were cooled to 10° C. in a condenser (3) in order to condense isopropyl acetate, and a mixture (C) containing the condensed isopropyl acetate, etc. was mixed with the liquid phase mixture(D).

The composition of the mixture(E) consisted to 71% of isopropyl acetate, to 25% of acetic acid and to 4% of other ingredients.

The mixture(E) was supplied into a first distillation column(5) which has 20 stages in the concentration portion and 20 stages in the collection portion. Distillation in column(5) was carried out at a reflux ratio of 30, so that the amounts in it of isopropanol, isopropyl ether and the olefins having a carbon number of 7 were decreased to approximately 500 ppm which is a specified value in a column-bottom mixture(I).

The column-bottom mixture(I) was supplied into a third distillation column(7). The composition of the distillate(F) in the first distillation column(5) consisted to 83% of isopropyl acetate, to 16% of low-boiling point ingredients which included isopropyl alcohol, isopropyl ether, and olefins having carbon number of 7, and to 1% of water.

Where the distillate(F) is disposed of without any treatment, the loss of isopropyl acetate would correspond to 7% based on the amount of the starting materials.

Accordingly, the distillate(F) was supplied into a second distillation column(6) in order to collect isopropyl acetate.

The second distillation column(6) was equipped with 20 stages in the concentration portion and 20 stages in the collection portion.

The distillation in the column(6) was carried out in a reflux ratio of 30, whereby the low-boiling point ingredients were concentrated to within the range of from 16% to 70% or so.

The distillate(G) in the first distillation column(6) was burned.

The column-bottom mixture(H) was supplied into the middle portion of the first distillation column(5). By carrying out the distillation with the use of the second distillation column(6), the loss of isopropyl acetate was decreased to approximately 0.7% based on the amount of the starting materials.

The column-bottom mixture(I) discharged from the first distillation column(5) was supplied into the third distillation column(7) having 40 stages in the concentration portion and 20 stages in the collection portion.

The third distillation column(7) was carried out in a reflux ratio of 1, so that an isopropyl acetate product(J) having a purity of 99.9% was distilled off at the column top.

After that, the column-bottom mixture(K) discharged from the third distillation column(7) was supplied into a fourth distillation column(8) in order to collect the unreacted acetic acid.

Collection of the unreacted acetic acid(M), removal of high-boiling point ingredients(N) and removal of low-boiling-point ingredients(L) were carried out with 20 stages in the concentration portion and 20 stages in the collection portion.

In the fourth distillation column(8), unreacted acetic acid and olefins having a carbon number of 9 were distilled off as an azeotropic mixture(L) from the column top, and the high-boiling-point ingredients(N) were discharged from the column bottom while a mixture(M) composed of acetic acid and sec-butyl acetate was discharged from a side stream line.

The mixture(M) was recirculated to the reaction vessel(1), whereby the loss of acetic acid was 0.8% based on the amount of the starting acetic acid.

EXAMPLE 2

Same procedures as described in Example 1 were repeated, except that there was used a crude propylene which contains 69.0% of propylene, 29.0% of propane and 2.0% of olefins having a carbon number of 4, etc.

The composition of the mixture(E) consisted to 71% of isopropyl acetate, to 25% of acetic acid and to 4% of other ingredients.

The same refining procedures in Example 1 were repeated to obtain an isopropyl acetate product having a purity of 99.9%.

It was confirmed that the quality of the isopropyl acetate product is not adversely affected despite lowering of the purity in a starting crude propylene.

The mixtures (A) to (P) in Examples 1 and 2 show the composition of the liquid or gas described below.

(A): isopropyl acetate, acetic acid, propylene, isopropyl alcohol, isopropyl ether, olefins having a carbon number of 7, olefins having a carbon number of 9, acetates, inert gasses such as propane, etc.

(B): propylene, inert gasses, isopropyl acetate, isopropyl alcohol, isopropyl ether, olefins having a carbon number of 7, etc.

(C): isopropyl acetate, isopropyl alcohol, isopropyl ether, olefins having a carbon number of 7, etc.

(D): isopropyl acetate, acetic acid, isopropyl alcohol, isopropyl ether, olefins having a carbon number of 7, olefins having a carbon number of 9, acetates, etc.

(E): isopropyl acetate, acetic acid, isopropyl alcohol, isopropyl ether, olefins having a carbon number of 7, olefins having a carbon number of, acetates, etc.

(F): isopropyl alcohol, isopropyl ether, olefins having a carbon number of 7, isopropyl acetate, etc.

(G): isopropyl ether, olefins having a carbon number of 7, isopropyl acetate, isopropyl alcohol, etc.

(H): isopropyl acetate, olefins having a carbon number of 7, etc.

(I): isopropyl acetate, acetic acid, olefins having a carbon number of 9, acetates, etc.

(J): isopropyl acetate having high purity[product]

(K): acetic acid, sec-butylacetate, olefins having a carbon number of 9, esters of olefins having a carbon number of 9 and minor amounts of isopropyl acetate, etc.

(L): acetic acid, olefins having a carbon number of 9, esters of olefins having a carbon number of 9 and minor amounts of isopropyl acetate, etc.

(M): acetic acid and sec-butylacetate, etc.

(N): high-boiling-point ingredients such as esters of olefins having a carbon number of 9, etc.

(O): propylene, inert gasses, etc.

(P): acetic acid and propylene which are starting materials and mixture(M)

It is noted that the crude propylene in Examples 1 and 2 was obtained by catalytically cracking naphtha.

EXAMPLE 3

Same procedures as described in Example 1 were repeated, except that there was used a crude propylene which contains 58% of propylene, 28% of propane, 7% of carbondioxide, 2% of methane, 3% of isobutane as olefins having a carbon number of 4 and 2% of other ingredients.

The crude propylene was obtained as a by-product in a process for the preparation of isobutene by the dehydrogenation of isobutane.

The composition of the mixture(E) consisted to 70% of isopropyl acetate, to 26% of acetic acid and to 4% of other ingredients.

The same refining procedures in Example 1 were repeated to obtain an isopropyl acetate product having a purity of 99.9%.

It was confirmed that the quality of the isopropyl acetate product is not adversely affected despite another starting crude propylene.

While the invention has been described in detail and with reference to specific embodiments thereof, it will be apparent to one skilled in the art that various changes and modifications can be made therein without departing from the spirit and scope thereof.

What is claimed is:

1. A process for the preparation of isopropyl acetate by the reaction of propylene having impurities with acetic acid which comprises the following steps:
   (a) separating a reaction mixture obtained in a reaction system into gas phase and liquid phase;
   (b) cooling said gas phase to separate into a condensate and a non-condensate;
   (c) mixing said condensate with said liquid phase to make a reaction crude mixture, and then charging said reaction crude mixture into a first distillation column to separate into a column-top-mixture having low-boiling-point ingredients and a column-bottom-mixture having high-boiling-point ingredients;
   (d) charging said column-top-mixture into a second distillation column to obtain a column-top-mixture containing low-boiling-point ingredients and a column-bottom-mixture containing isopropyl acetate;
   (e) recirculating said column-bottom-mixture in the second distillation column to the first distillation column while distilling off said column-top-mixture;
   (f) charging said column-bottom-mixture in the second distillation column into a third distillation column to obtain a column-top-mixture consisting essentially of isopropyl acetate and a column-bottom-mixture containing acetic acid and high-boiling-point ingredients;
   (g) charging said column-bottom-mixture in the third distillation column into a fourth distillation column to distill off a column-top-mixture containing minor amounts of acetic acid while recirculating a side-stream-mixture containing acetic acid to said reaction system and discharging a column-bottom-mixture containing high-boiling-point ingredients.

2. A process as set forth in claim 1, wherein said propylene includes propane and olefins having a carbon number of 4.

3. A process as set forth in claim 1, wherein said propylene is prepared by catalytically cracking petroleum.

4. A process as set forth in claim 1, wherein said propylene includes methane, ethane, propane, isobutane and olefins having a carbon number of 2 and 4.

5. A process as set forth in claim 1, wherein said propylene is prepared in a process for the preparation of isobutene by dehydrogenation of isobutane.

6. A process as set forth in claim 1, wherein said reaction system includes water.

7. A process as set forth in claim 1, wherein said column-bottom-mixture in the second distillation column is recirculated to the middle portion of the first distillation column.

8. A process as set forth in claim 1, wherein an acidic ion-exchange resin is used as a catalyst in said reaction system.

* * * * *